May 4, 1943. F. H. HOWARD Plant Pat. 581
ROSE PLANT
Filed Dec. 7, 1942
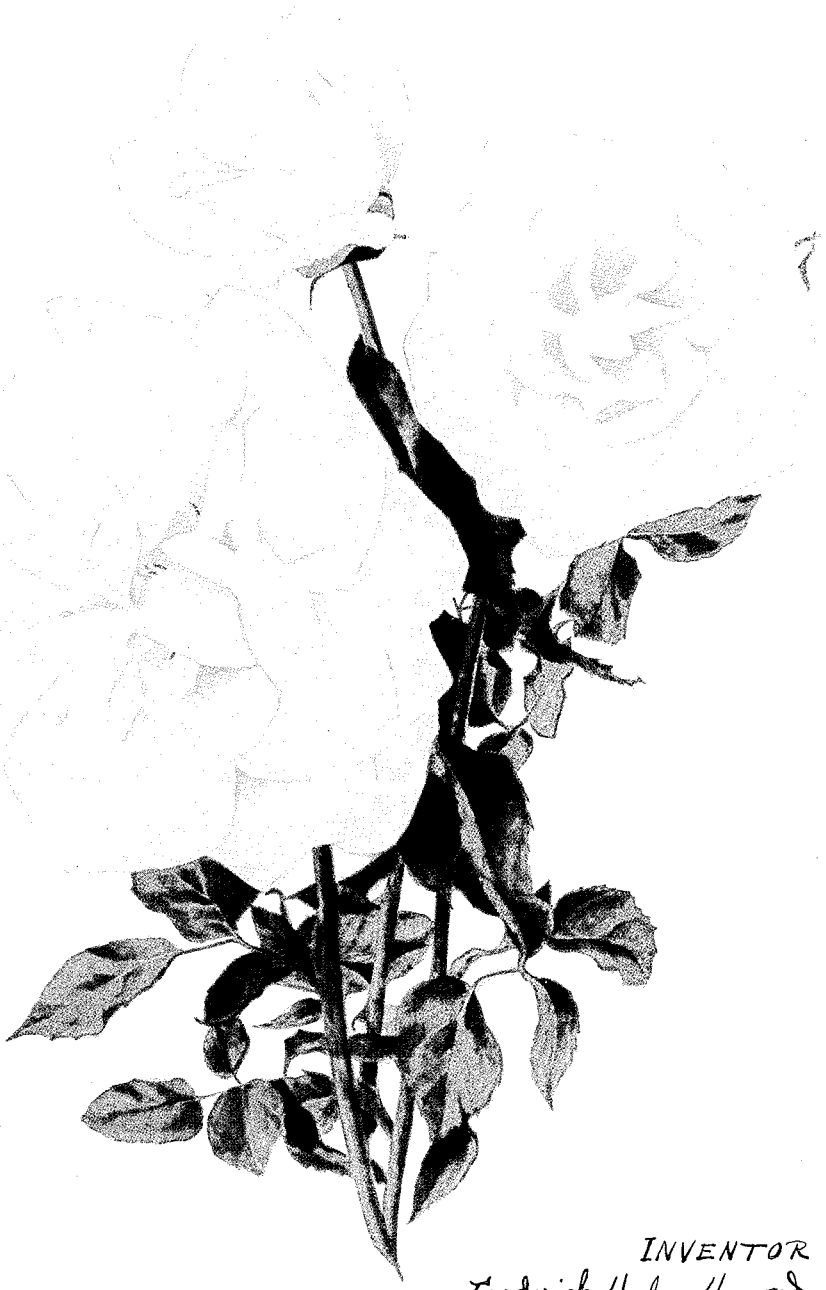
INVENTOR
Frederick Huber Howard
By Orville M. Kile
Plant Pat. Agt.

Patented May 4, 1943

UNITED STATES PATENT OFFICE

581

ROSE PLANT

Frederick Huber Howard, Montebello, Calif.

Application December 7, 1942, Serial No. 468,134

1 Claim. (Cl. 47—61)

My new invention relates to a new and distinct variety of hybrid tea rose plant, with particular reference to the growth and flower form. It is a particularly strong grower and is a prolific producer of large flowers of good form, color and fragrance. It is primarily a garden rose and has not been tested in greenhouses.

This new variety is the result of a cross made by me, of Mrs. J. D. Eisele by Glowing Sunset and has retained many of the good qualities of both parents. The color of the blossom contains much of the color of both parent varieties. The variety has been asexually reproduced and these outstanding characteristics appear to be firmly fixed.

The illustration which makes up a part of this application shows three specimens of this new variety in as nearly the true colors as the artist was able to make them. Allowance must be made for variation in specimens and those illustrated are typical.

Following is a detailed description of the plant and flower. Where plate numbers are given, Ridgway's Color Standards and Nomenclature is indicated. Where no plate number is given the ordinary dictionary meaning of the color is intended.

*The plant*

Growth: Upright, bushy; very strong and vigorous.

Disease resistance: Resistance to mildew and blackspot is unusually good.

Blooming habit: Very floriferous, continuous bloomer. Blossoms usually borne in clusters of three with the central blossom opening considerably in advance of the two lateral buds.

Stems: Very strong; heavy and stiff. New wood Yellowish Olive (Pl. XXX); older wood Dull Citrine (Pl. XVI)—both usually with reddish brown tinge on side next to sun. Moderate number of thorns.

*Thorns.*—Large; flat; sharp; slightly downward pointing; bright Rose Red (Pl. XII).

*Foliage.*—Small to medium in size. Terminal leaflet 1½ by 1¾ inches, lateral leaflet 1¼ by 1½ inches. Leaflets round to elliptical, with sharp apex and rounded base. Dark Cress Green (Pl. XXX) on upper surface; under surface between Light Bice Green (Pl. XVII) and Pois Green (Pl. XLI) with occasional red tinge. Smooth and glossy on upper surface. Edge very finely serrated.

Rachis: Grooved above and Neutral Red (Pl. XXXVIII); below, light green and smooth except for one or two small thorns.

Stipules: Short, clinging.

*The flower*

Bud: Before expanding, the bud is thick at the base but long and pointed. As calyx breaks, it is slightly less than an inch in length, but is 1½ to 1¾ inches long before it opens. The first show of color is between Rose Color and Rose Red (Pl. XII) with a touch of orange blended in. No color in Ridgway's Color Standards matches it but it might be called "oriental red." Just before expanding, the bud is somewhat as follows. The edges of the petals are then between Rose Color (Pl. XII) and Eugenia Red (Pl. XIII). The small base or aiglet is Strontian Yellow (Pl. XVI). The central and largest portion of the petal is a blend of these two colors. Sepals are simple and reflex early. Peduncle is short, strong, and tinged with red.

Blossom:

*Form.*—Exquisite high loose form, which some specimens retain. Other specimens open into loose, shaggy formation revealing a few of the stamens but scarcely ever opening into cupshape.

*Size.*—Large. 4 to 4½ inches across.

*Petalage.*—In October the average is about 30 petals.

*Color.*—The color of the blossoms varies considerably between specimens. Although the color of a typical blossom is not found in Ridgway's Color Standards, it may be described approximately as follows. Rose to pink on outer several rows, with inside petals having a coral tinge which brings them between Grenadine Pink (Pl. II) and Strawberry Pink (Pl. I). Each petal has a small yellow aiglet which is larger on the inner surface than on the outer surface. Later the whole flower is more nearly Rose Color (Pl. XII).

*Fragrance.*—Pronounced and delightful.

*Longevity.*—Excellent, especially as a cut flower. As an example, flowers shipped from California on the evening of October 13 and arriving in Washington, D. C., on the 16 (delayed by weather which prevented flying) were placed in water to revive them and then lasted nicely until the 18.

Petals:

*Shape.*—Outer petals are nearly round and deeply cupped. Edges smooth, seldom curling.

*Size.*—Outer petals are approximately 2¼ inches in each dimension.

*Arrangement.*—The open flower has a splendid petal arrangement wherein they are loose and upright with nearly every petal distinct.

*Behaviour.*—Petals drop cleanly when flower is spent.

Reproductive organs:

*Pistils.*—Many; tightly bunched; partly enclosed in calyx; rise above stamens because of their high position rather than their length. *Style*—White. *Stigma*—Red with light yellow to greenish tip.

*Stamens.*—Many; surround pistils. *Filaments*—uneven lengths; shorter than pistils; curved; light yellow with red tinge at base. *Anthers*—large; Light Cadmium (Pl. IV); attached at one of their ends rather than in the center.

*Comparisons*

The variety most like my new variety is Santa Anita, the subject of Plant Patent No. 539. However, these two varieties differ principally in the following respects.

1. Although both varieties have the same female parent, the male parent is different.
2. The new variety is a much stronger grower.
3. The new variety has greater resistance to mildew and blackspot.
4. The new variety is more prolific in production of flowers.
5. The color of the flowers of the two varieties differs—the Santa Anita being a soft silvery rose or deep pink while my new variety contains much coral and grenadine pink in its coloring as described.
6. The flower of my new variety has considerably more fragrance.
7. The flower of the new variety usually retains its high loose formation while Santa Anita opens into deep cupshape.

Having thus disclosed my invention, I claim:

The new and distinct variety of hybrid tea rose plant herein shown and described, characterized particularly by its adaptability to garden growing; its strong growth; its resistance to mildew and blackspot; its strong, heavy stems; its long pointed bud; and its prolific production of large fragrant flowers of excellent loose form and distinctive Rose Red to Grenadine Pink color as indicated.

FREDERICK HUBER HOWARD.